(12) United States Patent
Hu et al.

(10) Patent No.: US 11,642,293 B2
(45) Date of Patent: May 9, 2023

(54) COMPOSITION FOR CARING FOR SKIN, METHOD AND USE THEREOF

(71) Applicant: L'OREAL, Paris (FR)

(72) Inventors: Xiaoying Hu, Shanghai (CN); Runshuang Lu, Shanghai (CN); Lingling Sun, Shanghai (CN); Xiuxia Wang, Shanghai (CN)

(73) Assignee: L'OREAL, Paris (FR)

( * ) Notice: Subject to any disclaimer, the term of this patent is extended or adjusted under 35 U.S.C. 154(b) by 288 days.

(21) Appl. No.: 16/754,255

(22) PCT Filed: Oct. 25, 2017

(86) PCT No.: PCT/CN2017/107662
§ 371 (c)(1),
(2) Date: Apr. 7, 2020

(87) PCT Pub. No.: WO2019/080005
PCT Pub. Date: May 2, 2019

(65) Prior Publication Data
US 2020/0276095 A1 Sep. 3, 2020

(51) Int. Cl.
*A61K 8/368* (2006.01)
*A61K 8/9789* (2017.01)
(Continued)

(52) U.S. Cl.
CPC ............. *A61K 8/368* (2013.01); *A61K 8/345* (2013.01); *A61K 8/416* (2013.01); *A61K 8/44* (2013.01);
(Continued)

(58) Field of Classification Search
CPC .......... A61Q 19/00; A61Q 1/00; A61Q 17/04; A61Q 19/08; A61Q 1/02; A61Q 90/00; A61Q 1/14; A61Q 5/00; A61Q 19/02; A61Q 19/007; A61Q 5/12; A61Q 19/10; A61Q 1/10; A61Q 19/008; A61Q 19/04; A61Q 5/06; A61Q 5/10; A61Q 1/025; A61Q 1/04; A61Q 1/12; A61Q 17/00; A61Q 19/005; A61Q 5/002; A61Q 5/02; A61Q 5/065; A61Q 7/00; A61Q 1/06; A61Q 19/06; A61Q 3/00; A61K 8/27; A61K 8/28; A61K 8/29; A61K 8/604; A61K 2800/262; A61K 8/03; A61K 8/33; A61K 8/345; A61K 8/368; A61K 8/416; A61K 8/44; A61K 8/73; A61K 8/735; A61K 8/737; A61K 8/922; A61K 8/9789; A61K 2800/10; A61K 2800/43; A61K 2800/54; A61K 2800/591; A61K 2800/594; A61K 8/31; A61K 8/361; A61K 8/365; A61K 8/58; A61K 8/63; A61K 8/675; A61K 8/676; A61K 8/72; A61K 8/89; A61K 8/891; A61K 8/892; A61K 8/898; A61K 8/925; A61K 2800/412; A61K 8/0245; A61K 8/0279; A61K 8/19; A61K 8/8152; A61K 8/06; A61K 8/062; A61K 8/37; A61K 2800/21; A61K 8/8158; A61K 8/86; A61K 8/895; A61K 8/90; A61K 8/152; A61K 8/35; A61K 2800/413; A61K 2800/48; A61K 8/375; A61K 8/894; A61K 2800/782; A61K 8/0216; A61K 8/342; A61K 8/602; A61K 8/068; A61K 8/39; A61K 8/466; A61K 8/585; A61K 8/60; A61K 8/731; A61K 2800/88; A61K 8/0295; A61K 8/042; A61K 8/606; A61K 8/87; A61K 8/92; A61K 8/99; A61K 2800/522; A61K 2800/87; A61K 2800/872; A61K 48/00; A61K 8/0208; A61K 8/04; A61K 8/11; A61K 8/8141; A61K 2300/00; A61K 2800/28; A61K 2800/59; A61K 8/02; A61K 8/0204; A61K 8/14; A61K 8/20; A61K 8/34; A61K 8/347; A61K 8/442; A61K 8/49; A61K 8/4993; A61K 8/678; A61K 8/8117; A61K 8/8147; A61K 8/9728; A61K 8/9794; A61K 9/1075; A61K 2800/30; A61K 2800/31; A61K 2800/436; A61K 2800/52; A61K 2800/596; A61K 2800/84;
(Continued)

(56) References Cited

U.S. PATENT DOCUMENTS 5,871,758 A 2/1999 Nagy et al.
2010/0215603 A1* 8/2010 Kanda ..................... A61Q 5/00
514/171

(Continued)

FOREIGN PATENT DOCUMENTS

CN 105473185 A 4/2016
FR 2 663 847 A1 1/1992
WO WO 2004/014325 A1 2/2004

OTHER PUBLICATIONS

International Search Report and Written Opinion dated Aug. 1, 2018 in PCT/CN2017/107662 filed on Oct. 25, 2017.
(Continued)

*Primary Examiner* — Audrea B Coniglio
*Assistant Examiner* — Audrea Buckley
(74) *Attorney, Agent, or Firm* — Oblon, McClelland, Maier & Neustadt, L.L.P.

(57) ABSTRACT

A composition comprising at least two visually distinguishable phases, comprises at least one fatty phase with oil, at least one aqueous phase with hydrophilic gelling agent, and at least one compound chosen from N,N-dimethylglycine derivatives, alkyl(poly)glucosides, or a mixture thereof.

16 Claims, No Drawings

(51) Int. Cl.
    *A61K 8/34*     (2006.01)
    *A61K 8/41*     (2006.01)
    *A61K 8/44*     (2006.01)
    *A61K 8/60*     (2006.01)
    *A61K 8/73*     (2006.01)
    *A61K 8/92*     (2006.01)
    *A61Q 1/00*     (2006.01)
    *A61Q 19/00*     (2006.01)

(52) U.S. Cl.
    CPC ................ *A61K 8/604* (2013.01); *A61K 8/73* (2013.01); *A61K 8/735* (2013.01); *A61K 8/92* (2013.01); *A61K 8/9789* (2017.08); *A61Q 1/00* (2013.01); *A61Q 19/00* (2013.01)

(58) Field of Classification Search
    CPC .. A61K 31/7016; A61K 31/713; A61K 35/08; A61K 35/74; A61K 47/6907; A61K 47/6911; A61K 8/0254; A61K 8/044; A61K 8/40; A61K 8/42; A61K 8/463; A61K 8/4953; A61K 8/4973; A61K 8/4986; A61K 8/64; A61K 8/645; A61K 8/673; A61K 8/732; A61K 8/8135; A61K 8/8182; A61K 8/893; A61K 8/927; A61K 2800/5424; A61K 2800/5426; A61K 2800/5428; A61K 2800/5922; A61K 2800/882; A61K 2800/92; A61K 31/137; A61K 31/185; A61K 31/60; A61K 45/06; A61K 8/0241; A61K 8/046; A61K 8/26; A61K 8/36; A61K 8/38; A61K 8/43; A61K 8/447; A61K 8/4913; A61K 8/492; A61K 8/55; A61K 8/67; A61K 8/69; A61K 8/733; A61K 8/736; A61K 8/8164; A61K 8/817; A61K 8/85; A61K 8/88; A61K 8/899; A61K 8/91; A61K 8/965; A61K 9/1272; A61K 9/5089; A61K 9/7007; C08K 3/013; C08K 3/22; C08K 9/10

See application file for complete search history.

(56) References Cited

U.S. PATENT DOCUMENTS

| | | | |
|---|---|---|---|
| 2015/0190317 A1* | 7/2015 | Bossant | ................ A61K 8/604 514/25 |
| 2016/0256367 A1 | 9/2016 | Charbit | |

OTHER PUBLICATIONS

Extended European Search Report dated Jun. 7, 2021 in corresponding European Patent Application No. 17929810.4, 11 pages.
Anonymous: "Sunscreen ED—Dari Kuhn", ip.com, ip.com Inc., West Henrietta, NY,US, XP013142406, Feb. 4, 2011, pp. 1-296 and cover page.
Anonymous: "Foaming Skin Care Lotion", Internet Citation, XP002546857, Feb. 2009, pp. 1-2 Retrieved from the Internet: URL:http://www.degussa-personal-care.com/html/global/dynpdf.asp?typ=rezept&id=8423 [retrieved on Sep. 22, 2009].
Anonymous: "Rose Blossom Revitalizing Care", Database GNPD [Online] Mintel; XP055807563, Feb. 23, 2015, Database accession No. 3004071, pp. 1-5.
Combined Chinese Office Action and Search Report dated Mar. 16, 2022 in Patent Application No. 201780096273.2 (with English translation of Category of Cited Documents), 7 pages.

* cited by examiner

COMPOSITION FOR CARING FOR SKIN, METHOD AND USE THEREOF

TECHNICAL FIELD

The present invention relates to a composition for caring for and/or making up keratin materials, especially skin, which comprises at least two visually distinguishable phases. The invention also relates to a method for caring for and/or making up keratin materials using the composition.

BACKGROUND ART

Nowadays in the cosmetics market, there is not only a demand for products having a pleasant skin sensory upon application, as well as a visually unique and pleasant appearance to one another, but also an increasing demand for products with unique use experiences. The uniqueness in use experience plays a more and more important role in choosing cosmetic products.

Among all types of cosmetic products, in particular products for caring for the keratin materials, transparent appearance is always favored by the consumers, thanks to the clean and hydration perceptions linked thereof. Furthermore, a transformation of texture upon application becomes increasingly popular among the consumers. It is pleasant to observe cosmetic products presenting a visual transformation from one texture to another.

For years, efforts had been made to achieve the demands as described above. Cosmetic products with two visually distinguishable phases are seen on the market. Some of them contains an upper oily or fatty phase, and a lower aqueous phase. Before applying the products, the consumers are instructed to shake the bottle so as to obtain a mixture of the two phases. This type of use experience is very much favored by the consumers nowadays.

However, the use experience is yet to be improved.

Most of the products of this type turn to emulsion texture after shaking. This is to say, the products become opaque when shaking, this transformation is often irreversible. For few products which show a reversible transformation, the two or more phases do not present desired appearances. The phases are observed to be blur or opaque. Moreover, none of the above mentioned products shows a visually observable pleasant texture during transformation, i.e., a texture of oil droplets (or oil beads, oil globules) in an aqueous phase.

Therefore, there remains a need for a composition for caring for/making up the keratin materials, especially the skin, which shows a unique use experience as mentioned above, this experience is expected to be reversible. Besides, the composition presents a good appearance after undergoing multiple times of application.

Moreover, there is a need for a composition as described above, exhibiting a pleasant skin sensory (watery, smooth, soft and nutritious) on application.

Besides, the composition is also expected to be stable over time.

DISCLOSURE OF INVENTION

It is discovered that, in accordance to the present invention, a composition comprising at least two visually distinguishable phases, and comprising fatty phase, comprising at least one oil, and aqueous phase comprising at least one hydrophilic gelling agent(s) and at least 1% by weight of betaine, relative to the total weight of the composition, solves the above mentioned problems.

Thus, a subject of the present invention is a composition comprising at least two visually distinguishable phases, comprising:
a) at least one fatty phase, comprising at least one oil;
b) at least one aqueous phase comprising:
   i) at least one hydrophilic gelling agent; and
   ii) at least one compound chosen from the group consisting of, relative to the total weight of the composition:
   at least 1% by weight of N,N-dimethylglycine derivatives,
   from 0.01% to 2% by weight of alkyl(poly)glucosides,
   or a mixture thereof.

The other subject of the present invention is a process for caring for and/or making up keratin materials, in particular the skin, by applying to the keratin materials the composition of the present invention. Preferably, a step of shaking the composition before application is needed.

The term "keratin material" means the skin (of the body, face and around the eyes), hair, eyelashes, eyebrows, bodily hair, nails, lips or mucous membranes.

According to the present invention, the composition presents a unique use experience. The "use experience" refers to a transformation of the composition of the present invention during application.

More specifically, at first, the composition of the present invention comprises at least two visually distinguishable phases. By "visually distinguishable", it means that there is a clear and smooth boundary between two phases of the present invention, which is easily observed visually.

Preferably, the composition comprises an upper phase and a lower phase, which are visually distinguishable. More preferably the upper phase is a fatty phase, and the lower phase is an aqueous phase.

Then, after an external force is applied to the composition of the present invention, for example, shaking, the composition of the present invention presents a continuous aqueous phase and throughout the aqueous phase, numerous globules formed from a fatty phase (hereinafter sometimes referred to as oil beads or globules) are each individually dispersed.

In this connection, by "bead" or "globule", it means that there is a physical and visually distinguishable boundary between each bead or globule and the aqueous phase, wherein the boundary is smooth, rendering the globules having a homogeneous rounded or similar to round shape. Both of the aqueous phase and each globule or oil bead are preferably translucent or transparent, necessarily leading to an overall translucent or transparent appearance for the composition according to the present invention.

Further, the boundary between each oil bead or globule and the aqueous phase blinks under light by reflecting and refracting incident lights, and thus can be easily and distinctly seen with naked eyes. As a result, the composition according to the present invention may take a noble appearance like caviar as a whole.

Lastly, the composition of the present invention is stored without any external force after application. The appearance of the composition reverses back to its original appearance, preferably after storage of 8 hours at ambient temperature, more preferably after storage 6 hours at ambient temperature, even more preferably 1 hours. In other words, the transformation of the composition of the present invention is reversible.

The term "stability" means a composition that does not undergo any significant change in its structure or properties for at least one month after its manufacture and especially for at least two months after its manufacture.

As a result, the composition according to the present invention exhibits a unique use experience, i.e., a unique transformation during application, and furthermore the transformation is reversible. Moreover, the composition of the present invention provides to the skin pleasant skin sensory (watery, smooth, soft and nutritious) on application. Lastly, the composition of the present invention is stable over time.

DETAILED DESCRIPTION OF THE INVENTION

The present invention provides a composition for caring for and/or making up the keratin materials, comprising at least two visually distinguishable phases, comprising at least one fatty phase with oil(s), at least one aqueous phase with at least one hydrophilic gelling agent, and at least one demixing agent chosen from two ingredients.

Fatty Phase

The composition of the present invention comprises at least one fatty phase, comprising at least one oil.

The term "oil" refers to any fatty body in liquid form at room temperature (20-25° C.) and atmospheric pressure. These oils may be of animal, plant, mineral or synthetic origin.

The oils may be volatile or non-volatile.

The term "volatile oil" refers to any non-aqueous medium capable of evaporating from the skin or lips, in less than one hour, at room temperature (20-25° C.) and atmospheric pressure (760 mmHg).

More specifically, the volatile oil is a volatile cosmetic oil, liquid at room temperature. More specifically, a volatile oil has an evaporation rate of between 0.01 and 200 mg/cm$^2$/min, inclusive.

The term "non-volatile oil" is intended to mean an oil remaining on the skin or keratin fiber at ambient temperature and atmospheric pressure.

More specifically, a non-volatile oil has an evaporation rate strictly below 0.01 mg/cm$^2$/min.

To measure this evaporation rate, 15 g of oil or a mixture of oils to be tested are introduced into a crystallizer, 7 cm in diameter, placed on a scale located in a large 0.3 m$^3$ chamber temperature-controlled at a temperature of 25° C., and humidity-controlled with a relative humidity of 50%. The liquid is left to evaporate freely, without stirring, by providing ventilation with a fan (PAPST-MOTOREN, reference 8550 N, rotating at 2700 rpm) positioned vertically above the crystallizer containing the solvent, with the blades directed toward the crystallizer and at a distance of 20 cm from the base of the crystallizer. The mass of oil remaining in the crystallizer is measured at regular intervals. The evaporation rates are expressed in mg of oil evaporated per surface area unit (cm$^2$) and per time unit (minute).

The oils that are suitable for the present invention may be hydrocarbon-based, silicone-based or fluorine-based.

According to the present invention, the term "silicone oil" refers to an oil including at least one silicon atom, and in particular at least on Si—O group.

The term "fluorine oil" refers to an oil including at least one fluorine atom.

The term "hydrocarbon-based oil" refers to an oil containing primarily hydrogen and carbon atoms.

The oils may optionally include oxygen, nitrogen, sulfur and/or phosphorus atoms, for example, in the form of hydroxyl or acid radicals.

More preferably, the composition of the present invention comprises hydrocarbon oil(s).

Specifically, the volatile oils may be chosen from hydrocarbon oils having 8 to 16 carbon atoms, and in particular branched $C_8$-$C_{16}$ alkanes (also called isoparaffins or isoalkanes), such as isododecane (also called 2,2,4,4,6-pentamethylheptane), isodecane, isohexadecane, and, for example, the oils sold under the trade names Isopars® or Permethyls®.

It is also possible to cite, as a hydrocarbon volatile oil, linear $C_9$-$C_{17}$ alkanes, such as dodecane ($C_{12}$) and tetradecane ($C_{14}$), sold respectively under the names PARAFOL® 12-97 and PARAFOL® 14-97 (Sasol), and, as alkanes obtained according to the method described in the international application WO 2007/068371 A1, such as the undecane ($C_{11}$) and tridecane ($C_{13}$) mixture sold under the name CETIOL® UT (Cognis).

The non-volatile oils may, in particular, be chosen from among the non-volatile hydrocarbon oils.

It is possible to cite, as a non-volatile hydrocarbon oil:
hydrocarbon oils of animal origin, such as perhydrosqualene,
hydrocarbon oils of plant origin, such as phytostearyl esters, for instance phytostearyl oleate, phytostearyl isostearate and lauroyl/octyldodecyl/phytostearyl glutamate (AJINOMOTO, ELDEW PS203), diesters such as diisopropyl sebacate, triglycerides constituted of fatty acid esters of glycerol, in particular in which the fatty acids may have chain lengths ranging from $C_4$ to $C_{36}$, and in particular from $C_{18}$ to $C_{36}$, it being possible for these oils to be linear or branched, and saturated or unsaturated; these oils may in particular be heptanoic or octanoic triglycerides, shea oil, alfalfa oil, poppy seed oil, pumpkin oil, millet oil, barley oil, quinoa oil, rye oil, candlenut oil, passionflower oil, aloe oil, sweet almond oil, peach kernel oil, groundnut oil, argan oil, avocado oil, baobab oil, barrage oil, broccoli oil, calendula oil, camelina oil, canola oil, carrot oil, safflower oil, hemp oil, rapeseed oil, cotton seed oil, coconut oil, marrow seed oil, wheat germ oil, jojoba oil, lily oil, macadamia oil, corn oil, meadowfoam oil, St. John's Wort oil, monoi oil, hazelnut oil, apricot kernel oil, nut oil, olive oil, evening primrose oil, palm oil, blackcurrant seed oil, kiwi seed oil, grape seed oil, pistachio oil, pumpkin oil, winter squash oil, quinoa oil, musk rose oil, sesame oil, soya oil, sunflower oil, castor oil and watermelon oil, and mixtures thereof, or alternatively caprylic/capric acid triglycerides, for instance those sold by the StEarineries Dubois company or those sold under the names Miglyol 810®, 812® and 818® by the Dynamit Nobel company,
linear or branched hydrocarbons of mineral or synthetic origin, such as liquid paraffins and derivatives thereof, petroleum jelly, polydecenes, polybutenes, hydrogenated polyisobutene such as Parleam, squalane;
ethers oils having from 10 to 40 carbon atoms; for instance, ether oils of the formula (II),

$$R_3\text{—O—}R_4 \qquad \text{formula (II)}$$

In the formula (II):
$R_3$ and $R_4$, which may be identical or different, denote a linear or branched $C_6$-$C_{25}$ alkyl or alkenyl radical, $R_3$ and $R_4$ being chosen such that the ether is liquid at a temperature of less than or equal to 25° C.

According to the present invention, the term "ether oil" means oil that is liquid at room temperature (25° C.) comprising at least one ether functional group.

Preferably, the ether of formula (II) is chosen from compounds for which the radicals $R_3$ and $R_4$, which may be identical or different, denote a linear or branched $C_6$-$C_{12}$ alkyl or alkenyl radical.

More particularly, according to the present invention, the radicals $R_3$ and $R_4$ are identical alkyl radical.

Amongst ether of formula (II), the preferred dialkyl ether is chosen from di-n-hexyl ether, di-n-heptyl ether, di-n-octyl ether, di-n-nonyl ether, di-n-decyl ether, di-isodecyl ether, di-n-dodecyl ether, di-n-eteradecyl ether, di-n-hexadecyl ether, di-n-oxtadecyl ether, or a mixture thereof.

$R_3$ and $R_4$ preferentially denote a $C_8$ radical.

The dialkyl ethers that may be used according to the invention may be soluble or insoluble in the compositions, but are preferably insoluble.

These compounds may be prepared according to the process described in patent application DE 41 27 230.

Most preferably, a di-n-octyl ether (INCI name: dicaprylyl ether) that may be used in the context of the present invention. Such product is commercially available, for example those sold under the name Cetiol® OE by the company Cognis (BASF), or Rofetan® OE by the company Ecogreen Oleochemicals;
- synthetic esters, for instance oils of formula $R_1COOR_2$, in which $R_1$ represents a linear or branched fatty acid residue containing from 1 to 40 carbon atoms, and $R_2$ represents a hydrocarbon-based chain, in particular a branched chain, containing from 1 to 40 carbon atoms provided that $R_1$ or $R_2$ is greater than or equal to 10. The esters may in particular be selected from esters of fatty acid and of alcohol, for instance: cetostearyl octanoate, isopropyl alcohol esters, such as isopropyl myristate, isopropyl palmitate, ethyl palmitate, 2-ethylhexyl palmitate, isopropyl stearate or isostearate, isostearyl isostearate, octyl stearate, hydroxylated esters, for instance isostearyl lactacte, octyl hydroxy stearate, diisopropyl adipate, heptanoates, and especially isostearyl heptanoate, alcohol or polyalcohol octanoates, decanoates or ricinoleates, for instance propylene glycol dioctanoate, cetyl octanoate, tridecyl octanoate, 2-ethylhexyl 4-diheptanoate and palmitate, alkyl benzoate, polyethylene glycol diheptanoate, propylene glycol 2-diethylhexanoate, and mixtures thereof, $C_{12}$-$C_{15}$ alkyl benzoates, hexyl laurate, neopentanoic acid esters, for instance isodecyl neopentanoate, isotridecyl neopentanoate, isostearyl neopentanoate, or octyldodecyl neopentanoate, isononanoic acid esters, for instance isononyl isononanoate, isotridecyl isononanoate and octyl isononanoate, hydroxylated esters such as isostearyl lactate and diisostearyl malate;
- polyol esters and pentaerythritol esters, for instance dipentaerythrityl tetrahydroxystearate/tetraisostearate,
- esters of diol dimers and diacid dimers, such as Lusplan DD-DA5® and Lusplan DD-DA7®, sold by the nippon fine chemical company and described in the application US 2004-175338,
- copolymers of a diol dimer and of a diacid dimer and esters thereof, such as copolymers of dilinoleyl diol dimers/dilinoleic dimers and esters thereof, for instance Plandool-G,
- copolymers of polyols and of diacid dimers, and esters thereof, such as Hailuscent ISDA, or the copolymer of dilinoleic acid/butanediol,
- fatty alcohols that are liquid at ambient temperature, with a branched and/or unsaturated carbon chain having from 12 to 26 carbon atoms, for instance 2-octyldodecanol, isostearyl alcohol, oleyl alcohol, 2-hexyldecanol, 2-butyloctanol and 2-undecylpentadecanol,
- $C_{12}$-$C_{22}$, higher fatty acids, such as oleic acid, linoleic acid or linolenic acid, and mixtures thereof, and,
- dialkyl carbonates of the following formula (I):

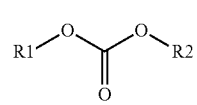

formula (I)

wherein $R_1$ and $R_2$, identical or different, each represents a linear or branched hydrocarbon chain comprising from 3 to 30 carbon atoms.

Preferably, according to an embodiment, in formula (I), $R_1$ and $R_2$, which are identical, represent a linear hydrocarbon chain comprising from 3 to 8 carbon atoms.

More preferably, the dialkyl carbonate is dicaprylyl carbonate.

In one embodiment, the carbonate is caprylyl carbonate. the two alkyl chains possibly being identical such as the dicaprylyl carbonate sold under the name Cetiol CC®, by Cognis.
- oils of higher molar mass having in particular a molar mass ranging from approximately 400 to approximately 10,000 g/mol, in particular from approximately 650 to approximately 10,000 g/mol, in particular from approximately 750 to approximately 7500 g/mol, and more particularly ranging from approximately 1000 to approximately 5000 g/mol. As oils of higher molar mass that can be used in the present invention, mention may in particular be made of the oils selected from:
- lipophilic polymers,
- linear fatty acid esters having a total carbon number ranging from 35 to 70,
- hydroxylated esters,
- aromatic esters,
- esters of $C_{24}$-$C_{28}$ branched fatty acids or fatty alcohols,
- oils of plant origin,
- and mixtures thereof; and
- mixtures thereof.

Preferably, the composition of the present invention comprises, as oils, at least one ether oil of formula (II), preferably dicaprylyl ether.

According to a preferred embodiment, the at least one oil (a) is present in an amount ranging from 1% to 50% by weight, preferably ranging from 5% to 30% by weight, relative to the total weight of the composition.

More preferably, the at least one fatty phase is present in an amount ranging from 1% to 50% by weight, preferably ranging from 5% to 30% by weight, relative to the total weight of the composition.

Aqueous Phase

According to the present invention, the composition comprises at least one aqueous phase. Said aqueous phase is preferably present in an amount ranging from 50% to 99% by weight, more preferably from 60% to 95% by weight of the total weight of the composition.

The aqueous phase may comprise water, at least one organic solvent miscible with water or mixtures thereof.

Preferably, the aqueous phase comprises at least one organic solvent miscible with water (at room temperature 25° C.) such as for example monoalcohols having from 2 to 6 carbon atoms such as ethanol, isopropanol; polyols notably having from 2 to 20 carbon atoms, preferably from 2 to 10 carbon atoms, and preferentially having from 2 to 6 carbon atoms, such as glycerol, propylene glycol, butylene glycol, pentylene glycol, hexylene glycol, caprylylglycol, dipropylene glycol, diethylene glycol; and mixtures thereof.

The aqueous phase of the composition of the invention preferably comprises water and at least a polyol, preferably butylene glycol, glycerol, or propylene glycol.

Preferably, the continuous aqueous phase comprises water, a mixture of polyols, preferably butylene glycol, glycerol, and propylene glycol.

Preferably, water is present in an amount ranging from 40% to 90% by weight, more preferably from 60% to 80% by weight of the total weight of the composition.

Preferably, the organic solvent(s) miscible with water is (are) present in an amount ranging from 5% to 80% by weight, more preferably from 7% to 20% by weight of the total weight of the composition.

Preferably, the aqueous phase, which may be in form of an aqueous gel phase, has a viscosity of from 50 mPa·s to 400 mPa·s (M2), preferably from 80 mPa·s to 350 mPa·s (M2), or specifically, a viscosity of from 100 mPa·s to 300 mPa·s (M2).

The viscosity is generally measured at 25° C. with a viscometer RHEOMAT RM 180 with Mobile 2 adapted to the viscosity of the composition to be tested (mobile is chosen for having a measure between 10 and 90 for UD, Unit Deviation), the measure being made after 10 mn rotating the mobile inside the composition, with a cisaillement from 200 $s^{-1}$. The UD values may then be converted in Poises (1 Poise=0.1 Pa·s) with a correspondence table.

Hydrophilic Gelling Agent(s)

For the purposes of the present invention, the term "hydrophilic gelling agent" means a compound that is capable of gelling the aqueous phase of the compositions according to the invention.

The gelling agent is hydrophilic and is thus present in the aqueous phase of the composition.

The gelling agent may be water-soluble or water-dispersible.

The hydrophilic gelling agent can be chosen from gelling agents of natural origin, or polysaccharides of biotechnological origin.

Gelling agents of natural origin or polysaccharides of biotechnological origin include algal extracts, gums, starches, dextrins, celluloses, pectins, chitosan and derivatives, polyholosides, or anionic polysaccharides.

According to a preferred embodiment, the hydrophilic gelling agent that is suitable to the present invention is selected from the group consisting of gums, or a mixture thereof.

The gums that are useful to the present invention are, for example, xanthan gum, gellan gum, guar gum and nonionic derivatives thereof (hydroxypropyl guar), gum arabic, konjac gum or mannan gum, gum tragacanth, ghatti gum, karaya gum, locust bean gum; agar gum, scleroglucan gums, carob gum (*Ceratonia siliqua* gum) and mixtures thereof; examples that may be mentioned include the xanthan gum sold under the name Keltrol® CG-T by the company CP Kelco, the gellan gum sold under the name the Kelcogel® CG LA by the company CP Kelco, the guar gum sold under the name Jaguar HP 105® by the company Rhodia; mannan gum, Konjac Gum® (1% glucomannan) sold by the company GfN, and mixture of carob gum and xanthan gum sold under the name Nomcort CG by the company Nisshin Oillio.

According to a preferred embodiment, the gelling agent is selected from gums, in particular xanthan gum, gellan gum, guar gum, carob gum, or a mixture thereof.

Preferably, the hydrophilic gelling agent may be present in a proportion of from 0.01% to 5% by weight, in particular from 0.02% to 1% by weight, relative to the weight of the composition.

Compound(s) ii)

The composition of the present invention comprises at least one compound chosen from the group consisting of N,N-dimethylglycine derivatives, alkyl(poly)glucosides, or a mixture thereof.

For the purpose of the present invention, these compounds, also known as demixing agents, allow the composition of the present invention to form a temporary dispersion composition upon shaking, and then separate to visually distinguishable phases upon standing still.

More specifically, such a temporary stage lasts less than 8 hours, preferably less than 6 hours, more preferably less than 1 hour.

In particular, when a composition of the present invention comprises at least one demixing agent as described above, it presents a unique use experience as expected. Thanks to the demixing agents, the composition of at least two visually distinguishable phases transforms to a pearly dispersion, wherein the fatty phase is dispersed in a continuous aqueous phase, wherein the fatty phase is in form of oil droplets as described above. This dispersion is temporary. After storing of the composition without any external force, preferably in 8 hours, more preferably 6 hours, even more preferably 1 hours, the dispersion separates to two visually distinguishable phases, which is same as the original appearance of the composition.

More preferably, during the whole process of use experience, the composition remains transparent or translucent, in particular transparent.

According to the present invention, the demixing agent is chosen from N,N-dimethylglycine derivatives, alkyl(poly)glucosides, or a mixture thereof.

The N,N-dimethylglycine derivatives that can be used in the present invention are the compounds of formula (A):

$$R(CH_3)(CH_3)N^+CH_2COO- \qquad \text{formula (A)}$$

wherein:
R represents a $C_1$-$C_6$ alkyl group.

Preferably in the formula (A), R represents a $C_1$-$C_4$ alkyl group, more preferably a methyl group.

The demixing agents of this type that can be mentioned is, for example, trimethylglycine, also known as betaine, which is sold under the name Aminocoat™ by the company Asahi Kasei.

Alkyl(poly)glucosides that are useful to the present invention are compounds of the formula (B):

$$R_7O-(G)_v \qquad (B)$$

in which:
$R_7$ represents a linear or branched, saturated or unsaturated alkyl group, containing from about 1 to 14 carbon atoms,
G represents a saccharide unit containing 5 or 6 carbon atoms, and
v denotes a value ranging from 1 to 15.

Preferably, the alkyl(poly)glycoside correspond to formula (B) in which:
G denotes glucose, fructose or galactose, preferably glucose.

The degree of polymerization of the alkyl(poly)glycoside as represented, for example, by the index v in formula (B) ranges on average from 1 to 15 and preferably from 1 to 4. This degree of polymerization more particularly ranges from 1 to 2 and better still from 1.1 to 1.5, on average.

The glycoside bonds between the saccharide units are 1,6- or 1,4-bonds; preferably 1,4-bonds.

The compounds of formula (B) that may be used in the present invention are especially represented by the products decyl glucoside sold by the company Cognis under the names Plantaren® (600 CS/U, 1200 and 2000) or Plantacare® (818, 1200 and 2000). It is also possible to use the products caprylyl/capryl glucoside sold by the company SEPPIC under the names Triton CG 110 (or Oramix CG 110) and Triton CG 312 (or Oramix® NS 10), the products sold by the company BASF under the name Lutensol GD 70, or those sold by the company Chem Y under the name AG10 LK.

When N,N-dimethylglycine derivatives of formula (A) is used as the demixing agent, it may present in an amount of 1.2% by weight or more, preferably from 1.2% to 10% by weight, more preferably from 1.5% to 5% by weight, relative to the total weight of the composition.

When the alkyl(poly)glucosides of formula (B) is used as the demixing agent, it may present in an amount ranging from 0.01% to 2%, preferably from 0.01% to 1% by weight, more preferably from 0.01% to 0.5% by weight, relative to the total weight of the composition.

According to a preferred embodiment, the composition of the present invention is substantially free of any other surfactants, which is different from the demixing agents described above.

By "free of" we intend to mean that the composition comprises less than 0.5% by weight, preferably less than 0.2% by weight of any other surfactants, relative to the total weight of the composition.

More preferably, the composition of the present invention does not comprise any other surfactant which is different from the demixing agents described above.

Adjuvants

In a known manner, the composition of the invention may also contain adjuvants that are common in cosmetics and/or dermatology, such as active agents, moisturizers, preserving agents, antioxidants, complexing agents, pH modifiers (acidic or basic), fragrances, fillers, bactericides, odour absorbers, colorants (pigments and dyes), film-forming polymers, and additional thickeners and/or gelling agents, different from the gelling agents as described above. These adjuvants are used in the usual proportions in the cosmetics field, for example from 0.01% to 30% relative to the total weight of the composition, and, depending on their nature, they are introduced into the aqueous phase or into the fatty phase, or alternatively into vesicles. These adjuvants and the concentrations thereof must be such that they do not modify the property desired for the composition of the invention.

Galenic Form

The composition of the present invention comprises at least two visually distinguishable phases.

By "visually distinguishable", it means that there is a clear and smooth boundary between two phases of the present invention, which is easily observed visually.

Preferably, the composition comprises an upper phase and a lower phase, which are visually distinguishable. More preferably the upper phase is a fatty phase, and the lower phase is an aqueous phase.

The composition can present a unique use experience. The galenic form of the present invention changes during the application.

More specifically, after an external force is applied to the composition of the present invention comprising at least two visually distinguishable phases as described above, for example, shaking, the composition of the present invention presents a continuous aqueous phase and throughout the aqueous phase, numerous globules formed from a fatty phase (hereinafter sometimes referred to as oil beads or globules) are each individually dispersed.

In this connection, by "bead" or "globule", it means that there is a physical and visually distinguishable boundary between each bead or globule and the aqueous phase, wherein the boundary is smooth, rendering the globules having a homogeneous rounded or similar to round shape. Both of the aqueous phase and each globule or oil bead are preferably translucent or transparent, necessarily leading to an overall translucent or transparent appearance for the composition according to the present invention.

Further, the boundary between each oil bead or globule and the aqueous phase blinks under light by reflecting and refracting incident lights, and thus can be easily and distinctly seen with naked eyes. As a result, the composition according to the present invention may take a noble appearance like caviar as a whole.

Lastly, the composition of the present invention is stored without any external force after application. The appearance of the composition reverses back to its original appearance. In other words, the transformation of the composition of the present invention is reversible.

Preferably, the at least two visually distinguishable phases of the present invention are transparent or translucent, during storage, or during application of the composition.

The transparency or translucency is observed by eyes. By "transparent or translucent" we intend to mean that it is easy to see through the composition of the present invention without any opacity, i.e., milky, blur, or white color. According to a preferred embodiment, the present invention relates to a composition comprising at least two visually distinguishable phases, comprising, the weight relative to the total weight of the composition:

a) at least one fatty phase, comprising from 5% to 30% by weight of at least one ether oils of formula (II), $$R_3-O-R_4 \quad \text{formula (II)}$$

wherein:

$R_3$ and $R_4$ are identical and denote a linear or branched $C_6$-$C_{12}$ alkyl or alkenyl radical, more preferably $R_3$ and $R_4$ are identical and denote $C_8$ radical;

b) at least one aqueous phase comprising:
  i) from 0.02% to 1% by weight of at least one hydrophilic gelling agent selected from gums; and
  ii) at least one compound chosen from the group consisting of, relative to the total weight of the composition:
    from 1.5% to 5% by weight of betaine,
    from 0.01% to 0.5% by weight of alkyl(poly)glucosides selected from the group consisting of trimethylglycine, decyl glucoside, caprylyl/capric glucoside, or a mixture thereof,
    or a mixture thereof.

Method and Use

The composition of the present invention can be prepared according to the general knowledge of a person skilled in the art.

Specifically, the composition of the present invention can be prepared by preparing separately the fatty phase and aqueous phase of the present invention, and bottling the two phases.

The composition of the present invention can be used for a non-therapeutic process, such as a process or method for making up/caring for the keratin materials, for example the skin, in particular the face and the lips, by applying to the keratin materials the composition of the present invention.

The present invention also relates to a use of the composition according to the present invention, as it is or in product for making up/caring for the skin, especially for the face and the body.

The terms "between . . . and . . . " and "ranging from . . . to . . . " should be understood as being inclusive of the limits, unless otherwise specified.

In the patent application, unless specifically mentioned otherwise, the contents are expressed on a weight basis relative to the total weight of the composition.

The examples that follow are aimed at illustrating the compositions and processes according to this invention, but are not in any way a limitation of the scope of the invention. All the parts and percentages in the examples are given on a weight basis and all the measurements were obtained at about 25° C., unless otherwise mentioned.

EXAMPLES

Example 1: Formulation Examples

The following formulas were prepared:

| INCI US | Invention formula 1 | Comparative formula A |
|---|---|---|
| SODIUM HYDROXIDE | 0.085 | 0.085 |
| ADENOSINE | 0.1 | 0.1 |
| BETAINE (Aminocoat ™ from Asahi Kasei) | 1.7 | 0 |
| 3-O-ETHYL ASCORBIC ACID | 1 | 1 |
| *MACADAMIA TERNIFOLIA* SEED OIL | 2 | 2 |
| SQUALANE | 5 | 5 |
| DICAPRYLYL ETHER (Cetiol ® OE from Cognis (BASF)) | 8 | 8 |
| *ROSA DAMASCENA* FLOWER WATER | 50 | 50 |
| XANTHAN GUM (Keltrol ® CG-T from CP Kelco) | 0.085 | 0.085 |
| GELLAN GUM (Kelcogel ® CG LA from CP Kelco) | 0.085 | 0.085 |
| SALICYLIC ACID | 0.3 | 0.3 |
| WATER | QS | QS |
| GLYCERIN | 3 | 3 |
| CAPRYLYL GLYCOL | 0.17 | 0.17 |
| PROPANEDIOL | 2.55 | 2.55 |

Comparative formula A does not contain any demixing agents as claimed.

| INCI US | Invention formulas | | | | |
|---|---|---|---|---|---|
| | 2 | 3 | 4 | 5 | 6 |
| SODIUM HYDROXIDE | 0.1 | 0.1 | 0.1 | 0.1 | 0.1 |
| SODIUM HYALURONATE | 0.01 | 0.01 | 0.01 | 0.01 | 0.01 |
| BETAINE (Aminocoat ™ from Asahi Kasei) | 1.7 | 1.7 | 1.7 | 1.7 | 0 |
| DECYLGLUCOSIDE (Plantacare ® 2000 from Cognis) | 0 | 0 | 0 | 0 | 0.05 |
| DICAPRYLYL ETHER (Cetiol ® OE from Cognis (BASF)) | 15 | 15 | 15 | 15 | 15 |
| XANTHAN GUM (Keltrol ® CG-T from CP Kelco) | 0 | 0.0425 | 0.05 | 0 | 0.1 |
| GELLAN GUM (Kelcogel ® CG LA from CP Kelco) | 0 | 0.0425 | 0 | 0 | 0 |
| XANTHAN GUM (and) *CERATONIA SILIQUA* (CAROB) GUM (Nomcort CG from Nisshin Oillio) | 0.068 | 0 | 0 | 0 | 0 |
| GUAR GUM (Jaguar HP 105 ® from Rhodia) | 0 | 0 | 0 | 0.25 | 0 |
| SALICYLIC ACID | 0.2 | 0.2 | 0.2 | 0.2 | 0.2 |
| WATER | QS | QS | QS | QS | QS |

| INCI US | Comparative formulas | |
|---|---|---|
| | B | C |
| SODIUM HYDROXIDE | 0.1 | 0.1 |
| SODIUM HYALURONATE | 0.01 | 0.01 |
| BETAINE (Aminocoat ™ from Asahi Kasei) | 1.7 | 0.4 |
| DICAPRYLYL ETHER (Cetiol ® OE from Cognis (BASF)) | 15 | 15 |
| XANTHAN GUM (Keltrol ® CG-T from CP Kelco) | 0 | 0.05 |
| SALICYLIC ACID | 0.2 | 0.2 |
| WATER | QS | QS |

Comparative B does not comprise hydrophilic gelling agent;

Comparative C contains less than 1% by weight of betaine, relative to the total weight of the composition.

The above listed formulas were formulated following conventionally known preparation.

Example 2: Evaluation Examples

The appearance, use experience, as well as the sensory of the above invention and comparative formulas were evaluated.

The use experience as well as the appearance were evaluated by following the steps of:
shake the formulas by hand, up to down 5 times;
observe the oil droplets in the formulas;
wait until formulas separate into two phases (within half day) again and observe:
1. the transparency of two phases;
2. the boundary of the two phases.

The performance score was based on these criteria:
5: excellent performance; 4: very good performance; 3: good performance; 2: not acceptable; 1: very poor performance.

The skin sensory of the invention and comparative formulas were evaluated by 3 panelists, by applying the formulas as a serum product on the facial skin, and scores of the sensory were given:
5: excellent sensory, hydration, soft skin feel; 4: good sensory, hydration and soft skin feel; 3: good, non-sticky feeling; 2: not acceptable, a bit oily, sticky feeling; 1: poor, very sticky and oily feeling.

The evaluation results were as follows:

| Item | Invention formulas | | | | | | Comparative formulas | | |
|---|---|---|---|---|---|---|---|---|---|
| | 1 | 2 | 3 | 4 | 5 | 6 | A | B | C |
| Appearance | 5 | 5 | 5 | 4 | 4 | 3 | 3 | 5 | 3 |
| Use experience | 4 | 5 | 5 | 4 | 3 | 4 | 2 | 1 | 2 |
| Sensory | 5 | 5 | 5 | 5 | 5 | 4 | 5 | 1 | 5 |

It was observed that: Invention formulas 1 to 6 show good properties in general; among which, invention formulas 2 and 3 are the most preferred embodiments, representing excellent appearance, use experience as well as sensory. Invention formula 5 shows a little bit bubble on the boundary of fatty phase and aqueous phase during and after shaking, yet acceptable; invention formula 6 shows a thickened boundary between the fatty phase and aqueous phase during and after shaking, yet acceptable.

Comparing to the invention formulas, the comparative formulas A to C are not satisfying in at least one of the properties:

Comparative formula A and C: appearance after shaking is a bit blur, not transparent, many bubbles occur on the boundary between the two phases during and after shaking, and not acceptable;

Comparative formula B: no oil droplets is formed during shaking, the sensory is very oily and greasy as the fatty phase is not dispersed in aqueous phase.

The invention claimed is:

1. A composition, comprising: at least two visually distinguishable phases, comprising:
   a) at least one fatty phase comprising at least one oil;
   b) at least one aqueous phase comprising:
   i) at least one hydrophilic gelling agent; and
   ii) at least one compound selected from the group consisting of, relative to the total weight of the composition:
      at least 1% by weight of at least one N,N-dimethylglycine,
      from 0.01% to 2% by weight of at least one alkyl(poly)glucoside, and
      mixtures thereof,
   wherein the at least one N,N-dimethylglycine is selected from a compound of formula (A):

$R(CH_3)(CH_3)N^1CH_2COO^-$  formula (A)

wherein R represents a $C_1$-$C_6$ alkyl group,
   wherein, after shaking, the composition has a continuous aqueous phase in which visually distinguishable globules formed from the at least one fatty phase are dispersed.

2. The composition according to claim 1, wherein the at least one oil is selected from hydrocarbon oils.

3. The composition of claim 1, wherein the at least one oil is present in an amount ranging from 1% to 50% by weight relative to the total weight of the composition.

4. The composition according to claim 1, wherein the fatty phase is present in an amount ranging from 1% to 50% by weight relative to the total weight of the composition.

5. The composition according to claim 1, wherein the aqueous phase is present in an amount ranging from 50% to 99% by weight relative to the total weight of the composition.

6. The composition according to claim 1, wherein the at least one hydrophilic gelling agent is selected from the group consisting of gelling agents of natural origin.

7. The composition according to claim 1, wherein the at least one hydrophilic gelling agent is present in an amount ranging from 0.01% to 5% by weight relative to the total weight of the composition.

8. The composition according to claim 1, wherein the at least one N,N-dimethylglycine is present in the composition and is selected from compounds of formula (A):

$R(CH_3)(CH_3)N^+CH_2COO^-$  formula (A)

wherein:
   R represents a $C_1$-$C_4$ alkyl group.

9. The composition according to claim 1, wherein the at least one N,N-dimethylglycine is present in the composition and is present in an amount of 1.2% by weight or more relative to the total weight of the composition.

10. The composition according to claim 1, wherein the at least one alkyl(poly)glucoside is present in the composition and is selected from compounds of the formula (B):

$R_7O\text{-}(G)_v$  (B)

in which:
    $R_7$ represents a linear or branched, saturated or unsaturated alkyl group, containing from about 1 to 14 carbon atoms,
    G represents a saccharide unit containing 5 or 6 carbon atoms, and
    v denotes a value ranging from 1 to 15.

11. The composition according to claim 1, wherein the at least one alkyl(poly)glucoside is present in the composition and is present in an amount from 0.01% to 1% by weight relative to the total weight of the composition.

12. A composition comprising at least two visually distinguishable phases, comprising, the weight relative to the total weight of the composition:
    a) at least one fatty phase, comprising from 5% to 30% by weight of at least one ether oils of formula (II), $R_3\text{—}O\text{—}R_4$  formula (II)

wherein:
    $R_3$ and $R_4$ are identical and denote a linear or branched $C_6$-$C_{12}$ alkyl or alkenyl radical,
    b) at least one aqueous phase comprising:
    i) from 0.02% to 1% by weight of at least one hydrophilic gelling agent selected from gums; and
    ii) at least one compound chosen from the group consisting of, relative to the total weight of the composition:
       from 1.5% to 5% by weight of betaine,
       from 0.01% to 0.5% by weight of alkyl(poly)glucosides selected from the group consisting of trimethylglycine, decyl glucoside, caprylyl/capric glucoside, or a mixture thereof,
    or a mixture thereof.

13. A process for making up/caring for the keratin materials, comprising applying to the keratin materials the composition according to claim 1.

14. The composition according to claim 1, wherein the at least one oil is selected from non-volatile hydrocarbon oils.

15. The composition according to claim 1, wherein the oil is selected from ether oils of formula (II), $R_3\text{—}O\text{—}R_4$  formula (II)

wherein:
    $R_3$ and $R_4$, identical or different, denote a linear or branched $C_6$-$C_{25}$ alkyl or alkenyl radical.

16. The composition according to claim 1, wherein the at least one hydrophilic gelling agent is selected from polysaccharides.

* * * * *